United States Patent
Beck et al.

(10) Patent No.: US 8,823,786 B2
(45) Date of Patent: Sep. 2, 2014

(54) METHOD AND APPARATUS FOR TESTING AN OPTICAL INVESTIGATION SYSTEM WITH A LIGHT SOURCE AND AN IMAGING SYSTEM

(75) Inventors: Gerd Beck, Wurmlingen (DE); Andre Ehrhardt, Wurmlingen (DE); Uwe Martin, Spaichingen (DE); Bernhard Gloeggler, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 312 days.

(21) Appl. No.: 12/969,916

(22) Filed: Dec. 16, 2010

(65) Prior Publication Data
US 2011/0149084 A1 Jun. 23, 2011

(30) Foreign Application Priority Data
Dec. 16, 2009 (DE) .......... 10 2009 058 663

(51) Int. Cl.
```
A62B 1/04      (2006.01)
A61B 1/045     (2006.01)
A61B 1/06      (2006.01)
A61B 1/00      (2006.01)
G01N 21/27     (2006.01)
A61B 5/00      (2006.01)
A61B 5/1495    (2006.01)
A61B 1/04      (2006.01)
```
(52) U.S. Cl.
CPC .............. *A61B 5/1495* (2013.01); *A61B 1/045* (2013.01); *A61B 1/0661* (2013.01); *A61B 1/00057* (2013.01); *G01N 21/278* (2013.01); *A61B 5/0084* (2013.01); *A61B 1/00186* (2013.01); *A61B 1/0646* (2013.01); *A61B 5/0071* (2013.01); *A61B 1/0638* (2013.01); *A61B 2560/0233* (2013.01); *A61B 1/043* (2013.01)
USPC .......................................................... 348/65

(58) Field of Classification Search
USPC ........................................................... 348/65
See application file for complete search history.

(56) References Cited

U.S. PATENT DOCUMENTS 6,356,342 B1 * 3/2002 Hyldahl et al. .................. 355/77
6,361,490 B1 * 3/2002 Irion et al. ..................... 600/175
(Continued)

FOREIGN PATENT DOCUMENTS

DE 19638809 A1 4/1998
DE 19855853 A1 6/2000
(Continued)

OTHER PUBLICATIONS

European Search Report; Application No. EP 10 19 4649; Mar. 22, 2011; 7 pages.

*Primary Examiner* — Chikaodili E Anyikire
*Assistant Examiner* — Leron Beck
(74) *Attorney, Agent, or Firm* — St. Onge Steward Johnston & Reens LLC

(57) ABSTRACT

A method for testing system with a light source and an imaging device for the optic investigation of an object in remitted light and fluorescent light, the imaging device positioned with respect to a reference surface within a hollow space of a test apparatus, the reference surface having an indicator area with a wavelength-dependent optical property, where the optical property essentially varies between a first focal point of a first product of a first predetermined illumination spectrum and a first predetermined transmission spectrum and a second focal point of a second product of a second predetermined illumination spectrum and a second predetermined transmission spectrum. The method includes illuminating the reference surface with illuminating light from the light source and determining which illumination spectrum and which transmission spectrum are present in an observation beam path on recording the image.

23 Claims, 4 Drawing Sheets

(56) References Cited

U.S. PATENT DOCUMENTS

| | | | |
|---|---|---|---|
| 7,072,036 B2 | 7/2006 | Jones et al. | |
| 7,714,911 B2 * | 5/2010 | Yoshida | 348/231.5 |
| 2006/0132660 A1 * | 6/2006 | Kurumisawa | 348/631 |
| 2007/0012885 A1 | 1/2007 | Montagu | |
| 2007/0282169 A1 * | 12/2007 | Tsujita | 600/160 |
| 2008/0038842 A1 * | 2/2008 | Ashley-Koch et al. | 436/501 |

FOREIGN PATENT DOCUMENTS

| | | |
|---|---|---|
| DE | 19962779 A1 | 6/2001 |
| DE | 20217340 U1 | 1/2003 |
| EP | 1728464 A1 | 12/2006 |
| WO | 9711636 A2 | 4/1997 |

* cited by examiner

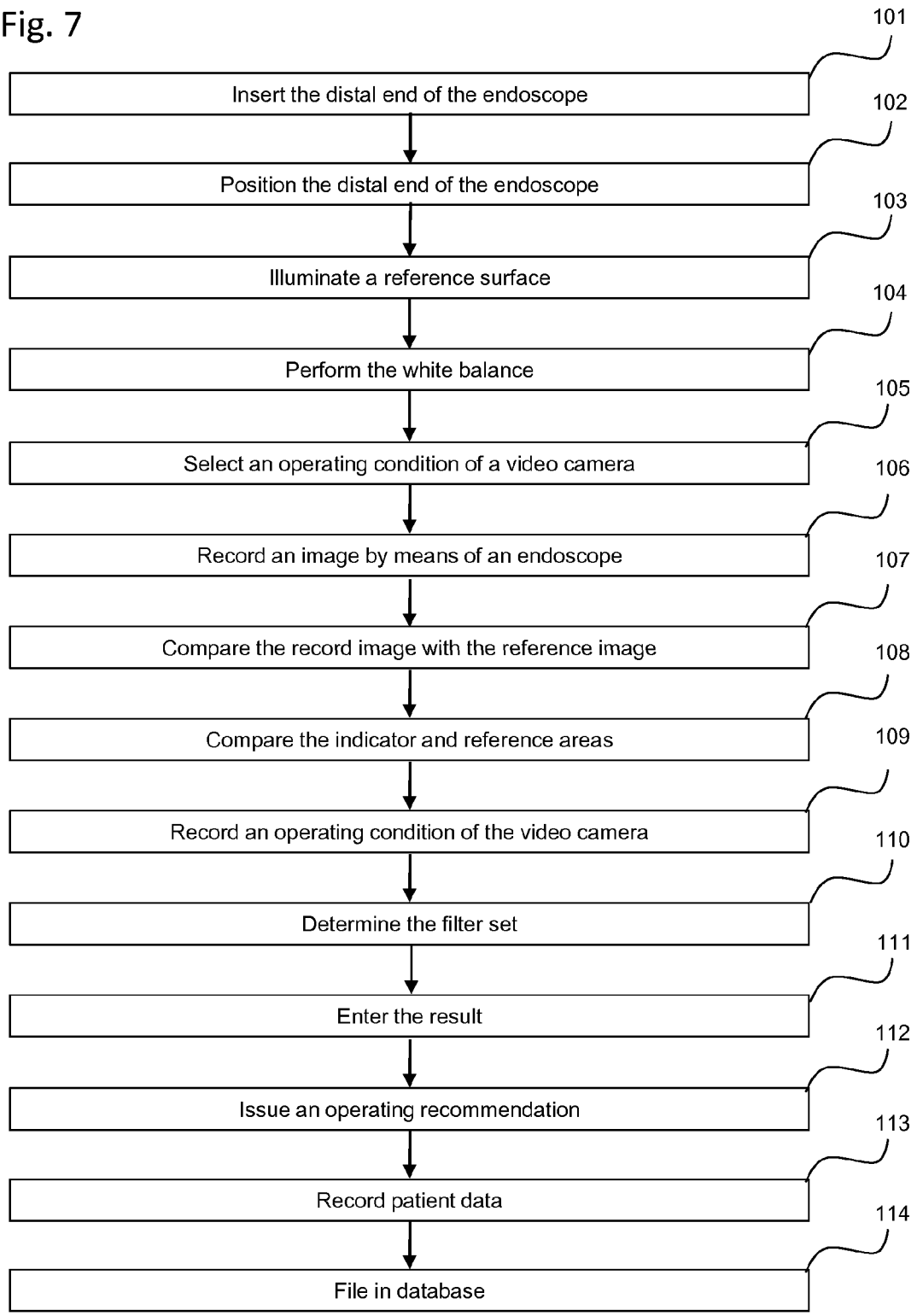

METHOD AND APPARATUS FOR TESTING AN OPTICAL INVESTIGATION SYSTEM WITH A LIGHT SOURCE AND AN IMAGING SYSTEM

CROSS-REFERENCE TO RELATED APPLICATIONS

The present application claims priority of German patent application No. 10 2009 058 663.6 filed on Dec. 16, 2009.

FIELD OF THE INVENTION

The present invention relates to a method for testing an optical investigation system with a light source and an imaging device for optical investigation of an object both within and outside the field of medicine. The present invention relates in particular to a method for testing an endoscopy system with a light source and an endoscope

BACKGROUND OF THE INVENTION

Endoscopy systems, consisting of an endoscope and a light source, are used for endoscopy in medical or non-medical applications—in the latter case also known as boroscopy. The light source can be integrated in the endoscope, in particular in its distal end, or can be present as a separate unit, which is optically coupled with an endoscope by a light conductor cable. Light from the light source emerges at the distal end of the endoscope and there illuminates an object to be investigated. Light remitted by the object is captured by a lens on the distal end of the endoscope and conducted onto a light-sensitive image sensor or conveyed, for example by means of an oriented bundle of lightwave conductors or a rod lens system, to the proximal end of the endoscope. In the latter case the light remitted by the object can be observed on the proximal end of the endoscope by an eyepiece or is recorded by means of a video camera. As an alternative or in addition to remitted light, light emitted by the object can also be observed, in particular fluorescent light.

The quality of an image recorded by an endoscopy system, in particular brightness, brightness-color contrast, signal-noise ratio, color fidelity and resolution or sharpness, depend on the observed object, in particular its optical properties, and above all on the endoscopy system. Relevant factors are, for example, the functionality of the light source, its radiant capacity or the light beam generated by it, the spectrum of generated light, in some cases the transmission properties of an employed light conductor cable and the coupling of the light conductor cable with the light source and with the endoscope, the functionality of the light transmission within the endoscope, the degree of effectiveness of the uncoupling of light from the light source out of the endoscope, the functionality or optical properties of the observation beam path in the endoscope, possibly including an oriented bundle of lightwave conductors or a rod lens system, the functionality of the eyepiece or video camera. Frequent sources of failure are, among others, the light source subjected to an alteration process, possibly the light conductor cable and its coupling to the light source and the endoscope, and the coupling of a video camera to the endoscope.

Fluorescent light is observed for medical-diagnostic purposes in particular. In photodynamic diagnostics (PDD), for example, a fluorescence of protoporphyrin IX induced by administered 5-aminolevulinic acid (ALA) is observed. Enrichment of ALA and thus also the intensity of the fluorescence depend on the condition of the tissue. In autofluorescence diagnostics (AF diagnostics) the fluorescence of bodily-produced fluorophores is observed, whose concentration is likewise dependent on the condition of the tissue. Fluorescent diagnostic methods are used in fields other than medicine as well.

To prevent remitted excitation light or illuminating light from outshining the fluorescence, an illumination filter is used in the illumination or excitation beam path between light source and object and in the observation beam path between object and video camera or eyepiece. The illumination filter is a short pass filter, which essentially transmits only the short wavelengths required to excite the fluorescence, but on the other hand primarily or almost exclusively reflects or absorbs longer wavelengths. A very reduced, but not disappearing, transmission in the blocking range is desired with many applications in order to receive, even without fluorescence, an image that has a low brightness but is visible. The observation filter is a long pass filter that transmits only wavelengths of fluorescence and reflects or absorbs short-wave illuminating light remitted by the object. Illumination or excitation filters can as a rule be manually or mechanically exchanged or changed. Observation filters can be replaceable or changeable, but in many case are firmly built into the endoscope. In urology, for example, for observation in white light, ALA or AF fluorescence, various endoscopes are used that, at least in the observation beam path, are optimized for their respective use or have a corresponding filter characteristic. The aforementioned sources of failure or influences on functionality of the endoscopy system include, in the case of observation of fluorescence, the combination of the illumination filter or spectrum of the light source on the one hand and of the observation filter on the other hand.

A corresponding problem exists with other optic investigation systems, which include an imaging device and a light source for optical investigation of medical and non-medical objects in remitted light and/or in fluorescent light. These include exoscopes, which for instance are used for diagnostics and for microsurgical procedures on or close to bodily surfaces.

DE 196 38 809 A1 describes a device for testing and/or adjusting a PDD or PDT system (PDT=photodynamic therapy) and/or for training on a system of this type. Positioned in a housing is a target, opposite to which a distal end of an endoscope can be mounted. The curvature of the target can correspond to the variable field curvature of an imaging unit of the endoscope. A photo element and light sources are provided in the target. The photo element records the illuminating strength of an illuminating light emitted from the endoscope. A control guides the light sources as a function of the illuminating strength recorded by the photo element.

DE 198 55 853 A1 describes an apparatus for testing and/or adjusting a PDD or PDT system and/or for training on a system of this type. The apparatus includes a luminescent phantom with a fluorescent dye. One end of an endoscope can be positioned opposite the luminescent phantom.

In the post-published DE 10 2009 043 696, an apparatus and a method for testing endoscopes are described. The apparatus includes a filter module with several perforations in which optic filters are positioned. The filter module is illuminated from one direction by the light source via a light conductor cable. From an opposite direction the light transmitted by the filter module is observed by means of an endoscope.

Each of the apparatuses and methods known by now, depending on concrete task assignments arising in practice, have advantages and disadvantages. For example, under some conditions and for a few applications none of the described apparatuses and methods allows a reliable testing of an optical investigation system, to determine which illumination filter and which observation filter are present. Also the apparatuses and methods described in DE 196 38 809 A1 and in DE 198 55 853 A1 do not permit, for example, any reliable distinction between similar sets of filter, such as filters for PDD and for AF diagnostics.

SUMMARY OF THE INVENTION

An object of the present invention consists in providing an improved method for testing an optical investigation system with a light source and an imaging device as well as an improved reference body.

This object is fulfilled through the contents of the independent claims.

Refinements are indicated in the dependent claims.

Embodiments of the present invention relate to the testing of an optical investigation system with a light source and an imaging device for optical investigation of an object in remitted light and fluorescent light, where the light source is configured to generate illuminating light with a first predetermined illumination spectrum or with a second predetermined illumination spectrum, and where an observation beam path of the imaging device comprises a first predetermined transmission spectrum and a second predetermined transmission spectrum. For example, the optical investigation system can include either illumination filters and observation filters for the PDD or illumination filters and observation filters for the AF diagnostics. The transmission spectrum of the PDD illumination filter and the transmission spectrum of the PDD observation filter comprise a small overlap; that is, the product of the transmission spectrum of the illumination filter and the transmission spectrum of the observation filter is clearly greater than zero only in a small wavelength range. This small wavelength area is also called the overlap area. Quantitatively the overlap area can be defined as the wavelength range in which the product of the transmission spectra of illumination and observation filters equals, for example, at least half or at least a third or at least a tenth of its maximum value. The transmission spectra of the illumination filter and of the observation filter for the AF diagnostics also comprise a small overlap. The overlap area for the filter set for the AF diagnostics is at greater wavelengths, however, than the overlap of the filter set for the PDD. The overlap areas are pushed closer together by about 25 nm.

Embodiments of the present invention are based on the idea of determining which illumination filter and which observation filter is present in an optic investigation system, illuminating a reference surface with an indicator area by means of the optic investigation system, and recording the light remitted by the reference surface or emitted on the basis of fluorescence by means of the optic investigation system. The indicator area has a wavelength-dependent optical property that essentially varies between the overlap area of the filter set for PDD and the overlap area of the filter set for AF diagnostics. The optical property is, for example, the wavelength-dependent remission factor or a fluorescence quantity yield that is dependent on the excitation wavelength.

In somewhat more general terminology, one of the ideas on which the present invention is based consists in distinguishing between two filter sets by employing a reference surface with an indicator area with an optical property that basically varies between a first focal point of a first product of the transmission spectrum of a first illumination filter and the transmission spectrum of a first observation filter and the second focal point of a second product of a transmission spectrum of a second illumination filter and a transmission spectrum of a second observation filter. The focal points of the products can be calculated without weighting the wavelengths or, for example, with weighting of the wavelengths according to the spectral sensitivity of the human eye or of a video camera. Instead of illumination filters that modify an originally broad spectrum, white in particular, of a light source, it is possible to use light sources that, without use of additional filters, generate the desired illumination spectrum, for example narrow-band light diodes, laser diodes or semiconductor lasers, other lasers, gas discharge lamps, and so on. A substantive change occurs, for example, if the remission factor or the fluorescence quantity yield at both focal points assumes values that differ from one another by ratios of at least 3:2 or 2:1 or 3:1.

A method refers to an optical investigation system with a light source and an imaging device for optical investigation of an object in remitted light and fluorescent light, where the light source is configured to generate illuminating light at least either with a first predetermined illumination spectrum or with a second predetermined illumination spectrum, and where an observation beam path of the imaging device comprises at least either a first predetermined transmission spectrum or a second predetermined transmission spectrum. With the method the imaging device is positioned with respect to a reference surface with an indicator area with a wavelength-dependent optical property, where the optical property essentially varies between a first focal point of a first product of the first predetermined illumination spectrum and the first predetermined transmission spectrum and a second focal point of a second product of the second predetermined illumination spectrum and the second predetermined transmission spectrum. The reference surface is illuminated with illuminating light from the light source, and an image of the reference surface is recorded by means of the imaging device. On the basis of the recorded image it is determined which illumination spectrum and which transmission spectrum were present in the observation beam path in recording the image.

The method is especially applicable to an endoscopy system with a light source and an endoscope for medical or non-medical applications and in particular for fluorescence diagnostics. The optic investigation system can alternatively include one of several alternative light sources, each of which generates various illumination spectra, or a light source whose illumination spectrum can be altered by mechanically or manually replacing an illumination filter. Alternatively, the optic investigation system can comprise one of several imaging devices whose observation beam paths have various transmission spectra, or an imaging device with an exchangeable observation filter. The reference surface is illuminated in particular by means of an illumination beam path integrated in the imaging device. The image of the reference surface can be recorded via an eyepiece by the human eye or by means of a video camera.

The indicator area can occupy any surface portion at all on the reference surface. In particular, the indicator area can be present as a spatially limited mark on an altogether clearly greater reference surface or can take up the entire reference surface. In the former case the indicator area can take the shape, for example, of one or more alphanumeric signs, a pictogram or another symbol.

The test method described here makes possible in astonishingly simple manner a test of an optic investigation system, in particular concerning the existing illumination spectrum or illumination filter and concerning the existing observation filter. Thus, through a purely qualitative or at most semi-quantitative evaluation of the recorded image of the reference surface with the indicator area, it becomes possible to make not just an identification of faulty filter combinations but also an investigation of reliable filter combinations for the PDD and AF diagnostics. It is impossible, as a rule, to tell with the naked eye whether a PDD illumination filter is combined with a PDD observation filter or an AF illumination filer is combined with an AF observation filter, without use of the indicator area proposed here. It is also not possible with the PDD, or is possible only for highly experienced medical personnel, to recognize if the optic investigation system erroneously comprises illumination and observation filters that are foreseen for AF diagnostics. The same holds true for an erroneous use of an optic investigation system with illumination and observation filters for PDD in AF diagnostics. At the same time, however, a PDD or an AF diagnostics with the wrong filter set in many cases provides a mistaken result. An incorrect result can have the most severe consequences. Ensuring, for example in PDD or in AF diagnostics, that the respective correct illumination and observation filters are used is thus of primary importance for quality assurance.

The test method described here is suited in many variants for optic investigation systems without video camera, because even with the naked eye on the eyepiece of the imaging device it is possible, on the basis of the image of the reference surface, to recognize on which illumination filter and which observation filter is present in the optic investigation system. The test method is thus suited even for those simpler optic investigation systems without video camera that are still frequently preferred by medical personnel.

In determining the illumination spectrum or illumination filter and the transmission spectrum in the observation beam path or the observation filter, the image recorded by means of the imaging device of the present optic investigation system can be compared with a reference image, in particular with several reference images. For example, reference images are provided that correspond to the various possible combinations of illumination filter and observation filter. In a comparison of the recorded image with the reference images, it is possible to determine with minor effort, quickly and reliably, to which reference image the recorded image is the most similar.

Alternatively or in addition, in the recorded image the reproduction of the indicator area can be compared with the reproduction of a reference area on the reference surface. The indicator area and the reference area, for example, are configured in such a way that the illumination spectrum and the transmission spectrum in the observation beam path can be identified on the basis of a comparison of the brightness and/or color tones of the indicator area and of the reference area. In particular, the indicator area is compared with several reference areas. A comparison of the reproduction of the indicator area with the reproduction of one or more reference areas in the recorded image is possible at the moment when the image is recorded, in particular with the eye on the eyepiece of the imaging device. In configuring the indicator area and/or the reference area or areas in the form of alphanumeric signs, pictograms or other symbols, the risk of an erroneous determination of the illumination spectrum and transmission spectrum in the observation beam path is further reduced.

The optical property of the indicator area and the corresponding optical property of the reference area can change in reverse manner between the first focal point and the second focal point. The result can be, for example, that in the recorded image the reproduction of the indicator area is brighter than the reproduction of the reference area when the optic investigation system comprises illumination filters and observation filters for PDD, and the reproduction of the reference area is brighter than the reproduction of the indicator area when the optic investigation system comprises illumination and observation filters for AF diagnostics.

The indicator area includes in particular an indicator filter whose filter edge or flank lies between the first focal point and the second focal point. The indicator filter is for example a wavelength-dependent absorbing coating in front of a reflecting surface or a wavelength-dependent reflecting filter. Behind or below the indicator filter or on the side of the indicator filter turned away from the imaging device, the indicator area can include a fluorescent surface. In this case the indicator filter is in particular a transmission filter, which has a high transmission degree at wavelengths lying above the filter edge, and has a high reflectance coefficient at wavelengths lying below the filter edge. Together with the color shift by the fluorescent surface, thus a color switch of the indicator area can be produced on the filter edge of the indicator filter. For example, the filter edge of the indicator filter is at 440 nm to 450 nm, and fluorescence in the green and/or red wavelength range of the fluorescent surface below the indicator filter can be excited by wavelengths in a range up to about 460 nm. Then the indicator area appears blue at illumination with a PDD illumination spectrum and observation by means of a PDD observation filter, and appears green to red at illumination by means of an AF illumination spectrum and observation by an AF observation filter. The two filter sets can thus be distinguished by the color of the reproduction of the indicator area in the recorded image.

Filters that correspond to, or are similar to, the illumination and observation filters for PDD or for AF diagnostics are particularly appropriate as indicator filters. The reflectance coefficient $R(\lambda)$ and the transmittance $T(\lambda)$ behave in complementary manner in many cases, at least approximately: $R(\lambda)=1-T(\lambda)$.

The image of the reference surface can be immediately recorded visually by means of an eyepiece or by a video camera. As already mentioned, the present invention makes possible a reliable verification of the correct filter combination even on a simple optic investigation system without video camera. The use of a video camera, in addition, makes possible an at least semi-quantitative evaluation of the recorded image.

If the optic investigation system includes a video camera, then before the image of the reference surface is recorded by the video camera, an operational condition of the camera can be entered at a predetermined value. For example, the illumination time and/or the amplification and/or white balance parameters of the camera are entered at predetermined values. Alternatively or in addition, it is possible to record the operational condition of the camera prevailing during the recording of the image by the camera. For example, automatically entered parameters such as the illumination time, the amplification and white balance parameter are recorded by the camera or a camera control with adaptation to the illumination situation, especially if they have not previously been entered at predetermined values. Recording the operational condition of the camera makes it possible to draw conclusions concerning brightness and spectral properties of the image of the reference surface generated by the camera by means of the imaging device.

With each of the methods described here, in addition, patient data can be recorded and information on the present illumination spectrum and the present transmission spectrum in the observation beam path of the optic investigation system and the patient data can be filed in a database. In the event the image of the reference surface was recorded immediately by the human eye on an eyepiece of the imaging device, this occurs in particular after medical personnel have entered the result of the previously described test on a user interface. If the image is recorded by means of a camera and is automatically evaluated, for example by the camera control, this can occur independently, without intervention by the medical personnel.

By integrating the test method with the recording and storing of the patient data, it can be ensured that with each medical-diagnostic use of the optic investigation system, it is also tested concerning its functionality and/or its other property and the result of the test is documented. The test method can thus become a reliable and non-manipulatable component of the quality control in regular clinical practices.

On recording the image by a video camera, a report can be generated after the test described above. This report names the particular illumination spectrum or illumination filter and the particular transmission spectrum of the observation beam path or the observation filter of the particular investigation system. Alternatively or in addition, the report can contain an operational instruction or an operational recommendation. For example, the report contains an order to exchange the illumination filter or the light source or the observation filter or the imaging device and thereafter to repeat the testing of the optical investigation.

The present invention can be implemented as a method or as a computer program with program code for executing or control of such a method if the computer program runs on a computer or processor. In addition, the invention can be implemented as a computer program product with a program code stored on a mechanically readable carrier (for example, an ROM, PROM, EPROM, EEPROM or Flash storage device, a CD-ROM, DVD, HD-DVD, Blue Ray DVD, diskette or hard drive) or in the form of firmware for executing one of the aforementioned methods if the computer program product runs on a computer, calculator or processor. In addition the present invention can be implemented as a digital storage medium (for example, ROM, PROM, EPROM, EEPROM or Flash storage device, CD-ROM, DVD, HD-DVD, Blue Ray DVD, diskette or hard drive) with electronically readable control signals that can interact with a programmable computer or processor system in such a way that one of the described methods is executed.

In addition the present invention can be implemented as a control device for an optical investigation system with an imaging device, in particular an endoscope, a video camera and a light source for optical investigation of an object, where the control device is configured to execute one of the described methods, or where the control device includes a computer program, a computer program product or a digital storage medium, as described in the preceding paragraph.

A reference body for testing an optical investigation system with a light source to generate a first predetermined illumination spectrum or a second predetermined illumination spectrum and an imaging device with an observation beam path with a first predetermined transmission spectrum or a second predetermined transmission spectrum includes a reference surface and an indicator area on the reference surface, where a wavelength-dependent optical property of the indicator area essentially changes between a first focal point of a first product of the first predetermined illumination spectrum and the second predetermined transmission spectrum and a second focal point of a second product of the second predetermined illumination spectrum and the second predetermined transmission spectrum.

The reference body is especially configured to execute one of the methods described above. In particular, the indicator area comprises an indicator filter as described above, where a fluorescent surface can be positioned below the indicator filter. In addition the reference surface can comprise a reference area, in particular several reference areas.

Embodiments are explained below with reference to the appended drawings

BRIEF DESCRIPTION OF THE DRAWINGS

FIG. 7 shows a schematic depiction of a flow diagram.

DETAILED DESCRIPTION OF THE INVENTION

Figure 1:
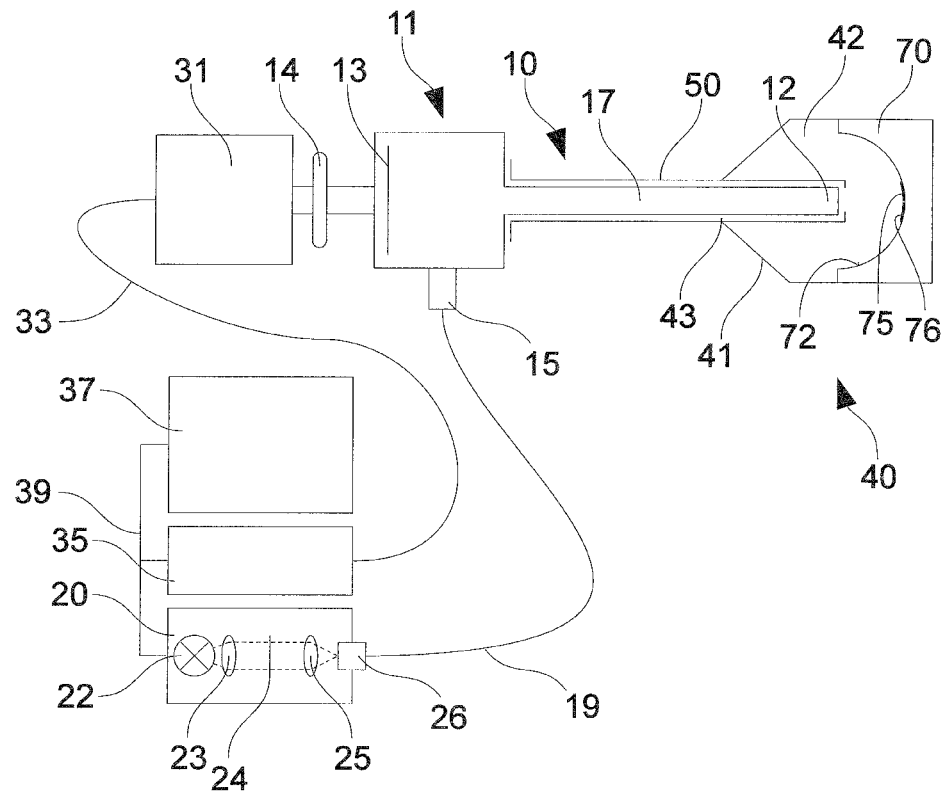
FIG. 1 shows a schematic depiction of an optic investigation system.

FIG. 1 shows a schematic depiction of an optic investigation system. The optic investigation system in this example is an endoscopy system, which can be applied, for example, in medical-diagnostic methods in urology and in other specialties. The endoscopy system includes an endoscope 10 with a proximal end 11 and a distal end 12. The endoscope 10 includes an illumination or excitation beam path and an observation beam path, which are not shown in detail in FIG. 1. The illumination beam path includes in particular one or more lightwave conductors to transmit illumination or excitation light from the proximal end 11 to the distal end 12 and a light outlet on the distal end 12 through which illumination light can exit from the distal end 12 of the endoscope 10 in order to illuminate an object to be observed. The observation beam path includes a light inlet on the distal end 12 of the endoscope 10, a lens to transmit observation light emitted from an observed object, from the distal end 12 to the proximal end 11, an observation filter 13 and an eyepiece 14. To transmit the observation light from the distal end 12 to the proximal end 11 of the endoscope 10, a rod lens system, for example, or an oriented bundle of lightwave conductors is provided in a shaft 17 of the endoscope 10. The endoscope 10 in addition comprises on its proximal end 11 a coupling 15 for mechanical and optical coupling of a light conductor cable 19 with the described illumination beam path in the endoscope 10.

The endoscope 10 is coupled with a light source apparatus 20 by the light conductor cable 19. The light source apparatus 20 includes a light source 22, for example a halogen lamp, a high-pressure gas discharge lamp, a light diode or a laser. In addition the light source apparatus 20 includes a first converging lens 23, an illumination filter 24 and a second converging lens 25. The light source 22 is coupled with the light conductor cable 19 by the first converging lens 23, the illumination filter 24, the second converging lens 25 and a coupling 26.

A video camera 31 is coupled mechanically or optically by the eyepiece 14 with the endoscope 10 and its observation beam path. The video camera 31 includes a light-sensitive image sensor, for example a CCD or CMOS sensor, to convert light falling onto the image sensor into analog or digital electrical signals. By means of a signal cable 33, the video camera 31 is coupled with a camera control unit 35, designated as CCU, to transmit analog or digital electrical or optical signals.

The light source apparatus 20, camera control unit 35, and a screen 37 are coupled with one another by a communication bus 39 or several separate signal lines. By means of the communication bus 39, additional apparatuses, not shown in FIG. 1, can be coupled with the light source apparatus 20, the camera control unit 35 and the screen 37 inside or outside the treatment area in which the endoscope system is installed; examples include a database, a keyboard, a computer mouse and other user interfaces.

Also shown in FIG. 1 is a test apparatus 40 with a light-insulated housing 41, a hollow space 42 in the light-insulated housing 41 and an aperture 43 to the hollow space 42. The distal end 12 of the endoscope 10 is introduced through the aperture 43 into the hollow space 42 of the test apparatus 40. A positioning device 50 located in the aperture 43 holds the shaft 17 of the endoscope 10 by form-locking or force-fitting, in such a way that the distal end 12 of the endoscope 19 is positioned in a predetermined position and in a predetermined direction in the hollow space 42. In addition, the positioning device 50, at least when the shaft 17 of the endoscope 10 is mounted in the positioning device 50, to a great extent prevents the penetration of light from the environment through the aperture 43 into the hollow space 42 in the housing 41.

In addition, a reference body 70 with a reference surface 72 is positioned in the hollow space 42 of the test apparatus 40. The reference surface 72 has predetermined optical properties and the spatial shape of a portion of a spherical surface or of a cylindrical mantle. The position foreseen for the distal end 12 of the endoscope 10 is situated in particular at the center point of this spherical surface or on the axis of symmetry of the cylindrical mantle. In particular, the main point on the object side, or the point of intersection of the optical axis with the object-side principal plane of the imaging device 10, stands at the center point of the spherical surface or on the axis of symmetry of the cylindrical mantle.

The reference surface 72 comprises several areas with various predetermined optical properties, each unchangeable or stable over time. One area of the reference surface 72 can be white or can have a remission factor that is essentially wavelength-independent in the spectral range visible to the human eye. Alternatively, one area of the reference surface 72 can be prevailingly in color or can have a remission factor that is wavelength-dependent in the spectral range visible to the human eye. Alternatively or in addition, one area of the reference surface 72 can be prevailingly fluorescent. Here, the wavelengths required for exciting fluorescence can be, for example, in the ultraviolet or, preferably for medical applications, in the blue spectral range and the emitted fluorescent light in the green, red or infrared spectral range. In the example shown in FIG. 1 the reference surface 72 is prevailingly white.

The reference surface 72 comprises an indicator area 75 and a reference area 76 each of which have optical properties different from the rest of the reference surface 72. The indicator area 75 and the reference area 76, with sharp edges or on the basis of their arrangement or shape, can simplify or make possible a focusing or adjustment of the focal length or the size of the visual field of the imaging device. In addition, the indicator area 75 and the reference area 76 have optical properties that simplify a determination of the transmission range of the illumination filter 24 and of the transmission spectrum of the observation filter 13. For this purpose the indicator area 75 and the reference area 76 each have a wavelength-dependent remission factor. This is described more fully below in connection with FIGS. 3 through 6.

The reference surface 72 consists, aside from the indicator area 75 and the reference area 76 on the reference surface 72, in particular of polytetrafluoroethylene PTFE, which is sold, for example, by DuPont under the brand name Teflon, or of silicon. Both PTFE and silicon be filled with white or color pigments or dyes.

Figure 2:
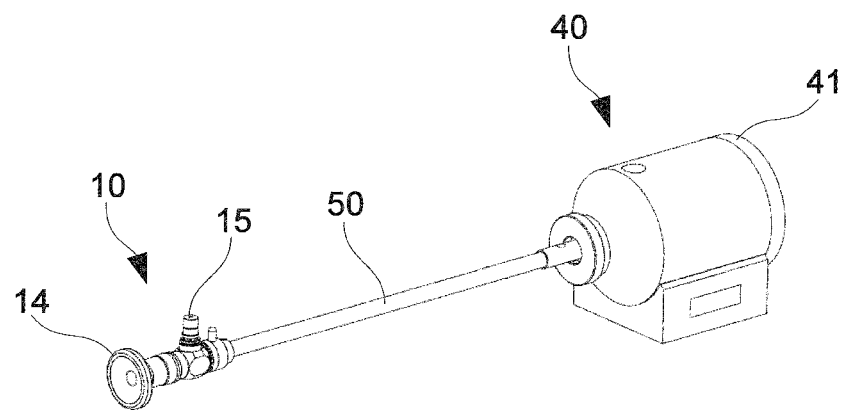
FIG. 2 shows a schematic depiction of an endoscope with a test apparatus.

FIG. 2 shows a schematic axonometric view of an endoscope 10 and of a test apparatus 40 that are similar to the endoscope and test apparatus that were presented above with reference to FIG. 1. Contrary to FIG. 1, no separate light source, video camera or other apparatuses are shown. The exact positioning of the distal end of the endoscope 10 in the test apparatus 40 is achieved in this example by form-locking between the positioning device 50 and the distal end 11 of the endoscope 10, in particular by means of a mechanical stop or a catch-locking connection.

The test methods described hereinafter are also applicable to optical investigation systems and test apparatuses that differ from those illustrated in FIGS. 1 and 2. For example, the test methods are applicable regardless of whether a light source and/or a video camera are separate units that can be coupled with the endoscope or are integrated in the endoscope at its proximal or distal end. In addition, the test methods are applicable when the excitation or illuminating light is conducted not by the endoscope or generally by the imaging device, but rather in other manner onto the object to be observed or onto the reference surface. The arrangement of illumination and observation filters can also differ from the examples presented above with reference to FIGS. 1 and 2. For the sake of greater clarity, reference numbers from FIGS. 1 and 2 are nevertheless used hereinafter by way of example.

The test method described hereinafter is applicable in particular when the foreseen application of the optic investigation system is PDD, AF diagnostics or another fluorescence diagnostic. For clarity, fluorescence, excitation and de-excitation spectra as well as transmission spectra of illumination and observation filters are described for fluorescence diagnostics. For example, the filters used for PDD and those for AF diagnostics differ from one another, yet can easily be confused with one another in visual observation. The test method described above can be modified in such a way that the filters being used can be identified.

Figure 3:
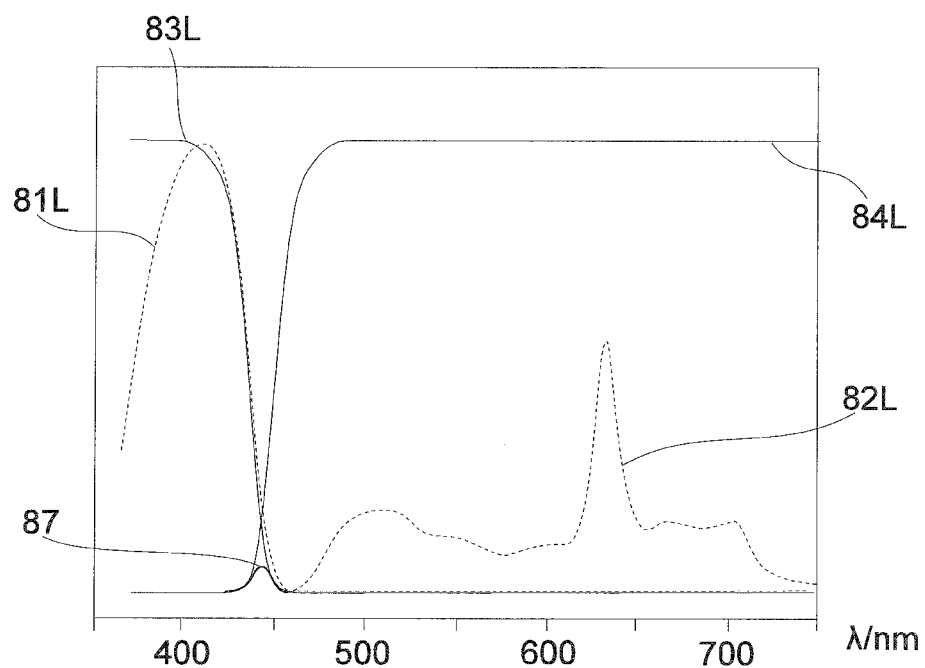
FIG. 3 shows a schematic depiction of several spectra.

FIG. 3 shows a schematic depiction of a fluorescence excitation spectrum 81L and of a fluorescence de-excitation spectrum 82L from fluorescence of protoporphyrin IX induced by 5-aminolevulinic acid (ALA). The wavelength $\lambda$ is assigned to the abscissa axis and quantity yield or intensity to the ordinate axis in arbitrary units. Also depicted are a transmission spectrum 83L of an appropriate illumination filter 24 and a transmission spectrum 84L of an appropriate observation filter 13. For the transmission spectra 83L and 84L, the transmittance degree in each case is assigned to the ordinate axis.

In addition, the product 87 of transmission spectra 83L, 84L or the transmission spectrum of the successively switched-on illumination and observation filters is depicted. The filter edges of the illumination filter 24 and of the observation filter 13 are selected so that the product of their transmission spectra in a small wavelength range is not zero, and is also designated as the overlap area. A small portion of the illuminating light that strikes the observed object can therefore be observed by the observation filter 13. The observed object therefore is also recognizable without fluorescence in (without wavelength displacement) remitted blue illumination light. Fluorescence, on the other hand, appears primarily in the green and red spectral range. Thus there is a clear color contrast between fluorescent and non-fluorescent areas of an object observed by means of the optic investigation system.

Figure 4:
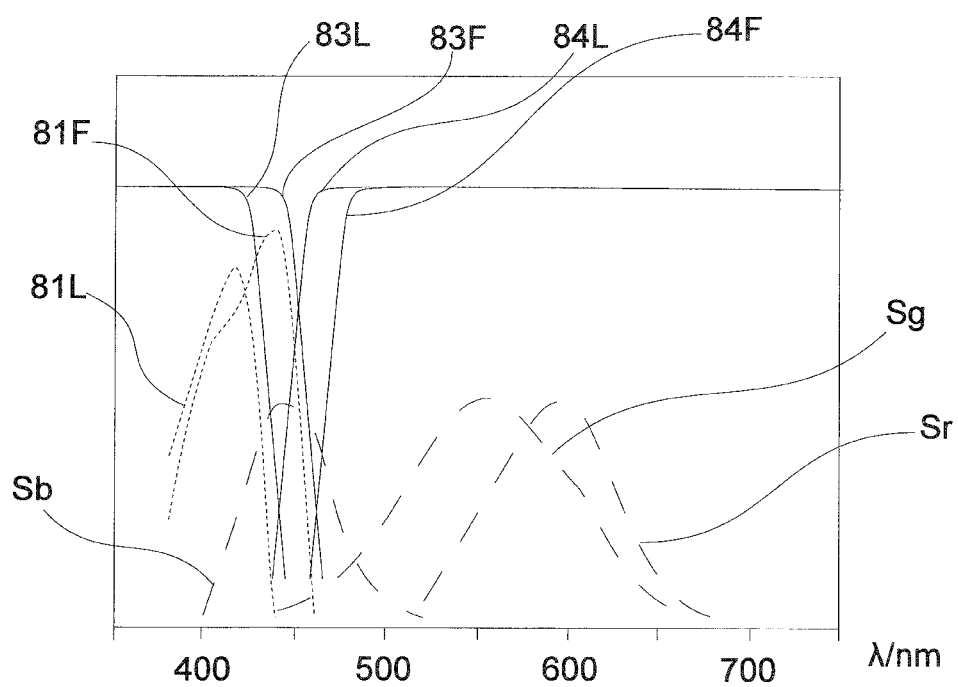
FIG. 4 shows a schematic depiction of additional spectra.

FIG. 4 is a schematic depiction of fluorescence-excitation spectra as well as transmission spectra of illumination and observation filters, which are used for various types of fluorescence diagnostics. The wavelength λ is plotted on the abscissa axis. In addition to the fluorescence-excitation spectrum 81L, the transmission spectrum 83L, the illumination filter and transmission spectrum 84L of the observation filter for PDD, the figure also shows the fluorescence-excitation spectrum 81F, the transmission spectrum 83F of the illumination filter and the transmission spectrum 84F of the observation filter for observing autofluorescence (AF) of tissue.

In addition, FIG. 4 shows spectral sensitivities Sb, Sg, Sr of the blue, green and red color receptors of the human eye. Because cameras as far as possible are adapted to the color reception of the human eye, as a rule they have similar spectral sensitivities or separate the color channels even more sharply. In comparing the transmission spectra 83L, 83F, 84L, 84F of the illumination and observation filters for PDD and AF with the spectral sensitivities of the color receptors of the human eye, it becomes clear that the small differences between the transmission spectra of the illumination and observation filters for PDD and AF are recognizable to the human eye only under good conditions in immediate comparison—which is seldom possible.

Figure 5:
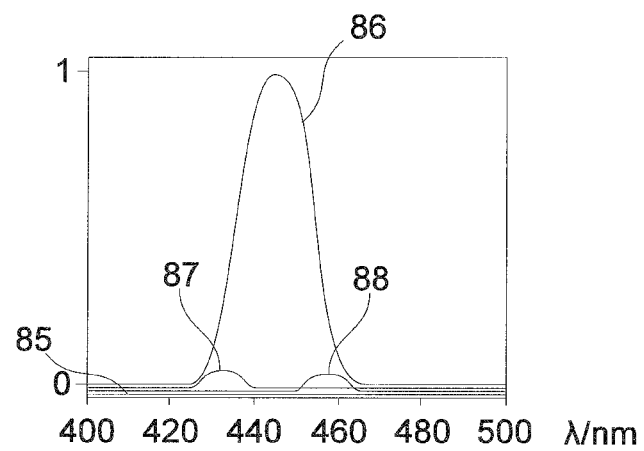
FIG. 5 shows a schematic depiction of products of transmission spectra.

FIG. 5 shows a schematic depiction of various products, each of a transmission spectrum of an illumination filter and of a transmission spectrum of an observation filter. The curves are vertically slightly pushed toward one another so that they can be distinguished more easily. In fact, all products at wavelengths around 400 nm and at wavelengths around 500 nm are close to zero.

The product 85 of the transmission spectrum 83L of the PDD illumination filter and the transmission spectrum 84F of the AF observation filter is very small or nearly zero for all wavelengths. Thus the AF observation filter is not transparent for remitted PDD excitation light.

The product 86 of the transmission spectrum 83F of the illumination filter for AF diagnostics and the transmission spectrum 84L of the observation filter for PDD is clearly greater than zero for wavelengths in the range from about 430 nm to about 460 nm. The PDD observation filter is thus transparent for remitted AF excitation light to a clearly visible degree.

The product 87 of the transmission spectrum 83L of the illumination filter for PDD and the transmission spectrum 84L of the observation filter for PDD is, as already shown above with reference to FIG. 4, not zero in a small wavelength range between about a 430 nm and about 440 nm. The PDD observation filter is slightly transparent for remitted PDD excitation light.

The product 88 of the transmission spectrum 83F of the illumination filter for AF and the transmission spectrum 84F of the observation filter for AF is not zero in a small wavelength range in the area of 460 nm. The AF observation filter is slightly transparent for remitted AF excitation light.

Regarding a white, non-fluorescent reference surface with an optic investigation system, it can thus be clearly distinguished under favorable circumstances whether a PDD illumination filter is combined with an AF observation filter or an AF illumination filter is combined with a PDD observation filter. In the first case, an extremely dark image is observed; in the second case, too bright an image is observed in comparison to correct combinations of illumination filter and observation filter. It can scarcely be distinguished whether an illumination filter for PDD is combined with an observation filter for PDD or an illumination filter for AF with an observation filter for AF. In both cases the image is approximately equally bright; the difference in wavelength in any case can be distinguished by the human eye in very good conditions in an immediate comparison.

Figure 6:
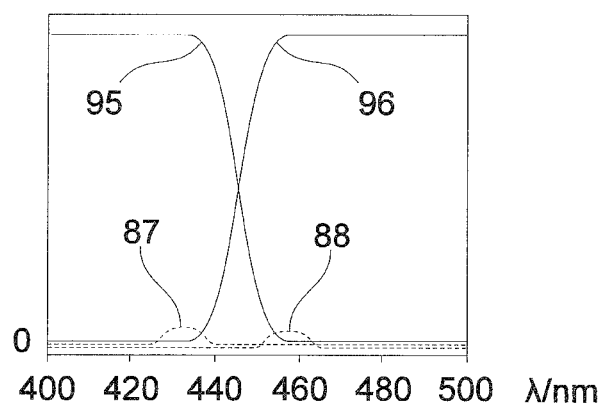
FIG. 6 shows a schematic depiction of additional transmission spectra.

FIG. 6 shows a schematic depiction of a reflection spectrum 95 of the indicator area 75 and of a reflection spectrum 96 of the reference area 76 on the reference surface 72. The abscissa shows the wavelength λ, the ordinate the reflectance coefficient in random units. In addition, the figure displays the product 87 of the transmission spectrum 83L of the illumination filter for PDD and the transmission spectrum 84L of the observation filter for PDD and the product 88 of the transmission spectrum 83F of the illumination filter for AF and the transmission spectrum 84F of the observation filter for AF. The reflectance spectra 95, 96 each comprise a flank or an edge at 440 nm to 450 nm. The reflectance coefficient 95 of the indicator area 75 has a high value at wavelengths below 440 nm and a small value at wavelengths greater than 450 nm. The reflectance coefficient 96 of the reference area 76 has a small value at wavelengths smaller than 440 nm and a large value at wavelengths greater than 450 nm.

If the reference surface 72 is illuminated with the indicator area 75 and the reference area 76 with the illumination filter 24 for PDD, the indicator area 75 appears clearly brighter through the observation filter for PDD than the reference area 76. If the reference surface 72 is illuminated by the illumination filter for AF, the indicator area 75 appears clearly darker through the observation filter for AF than the reference area 76. The test method described below is based on these different brightnesses.

The distal end 12 of the imaging device 10 is inserted into a hollow space 42 in a housing 41 of a test apparatus 40. A positioning device 50 holds the imaging device 10, in particular its distal end, by force- and/or form-locking to a predetermined position and in a predetermined direction in relation to the described reference surface 72 with the indicator area 75 and the reference area 76, which were described with reference to FIG. 6.

The reference surface is then illuminated by a light source 22 of a light source apparatus 20 with illuminating light and observed visually by the imaging device 10 or by means of a video camera. On the basis of the image of the reference surface thus acquired, it can be determined with which illumination spectrum the reference surface is illuminated or which illumination filter is present in the illumination beam path, and which transmission spectrum is present in the observation beam path. If both the indicator area 75 and the reference area 76 appear dark in the recorded image, then an illumination spectrum for PDD and an observation filter for AF are present. If the indicator area 75 appears clearly brighter than the reference area 76, then an illumination spectrum for PDD and an observation filter for PDD are present. If the reference area 76 appears clearly brighter than the indicator area 75, then an illumination spectrum for AF and an observation filter for AF are present. If both the indicator area 75 and the reference area 76 appear bright, then an illumination spectrum for AF and an observation filter for PDD are present.

The reference surface 72 described here with the indicator area 75 and the reference area 76 can be varied in many ways. For example, when only one distinction is desired between the two admitted filter combinations (PDD illumination filter and PDD observation filter or AF illumination filter and AF observation filter), the reference area 76 can be dispensed with. The indicator area 75 can even occupy the entire surface of the reference surface 72. Merely on the basis of recognizing whether the indicator area 75 appears bright or dark in the recorded image, it is possible to distinguish which of the two admitted filter combinations is present. The non-admitted filter combinations can be identified, for example, on the basis of other distinguishing features of the reference surface 72.

A color contrast can be generated alternatively to a brightness contrast or in addition to it. For example, the indicator area 75 comprises a transmission filter before a fluorescent surface, so that the degree of transmission of the indicator filter as well as the reflectance coefficient 76 from the example described above comprises a rising flank in the range of 440 nm to 450 nm. The reflectance coefficient R ($\lambda$) is approximately given as R($\lambda$)=1−T($\lambda$) and has approximately the shape of the reflectance spectrum 95 from the example described above. The fluorescent surface below or behind the indicator filter shows a fluorescence that can be excited by wavelengths less than 440 nm, so that the fluorescent light for example is in the green or red spectral range. Upon illuminating this indicator area with a PDD illumination spectrum, the latter is reflected without frequency displacement. Upon illuminating the indicator area with AF illuminating light, a part of the illuminating light (its long-wave portion) will fall through the indicator filter onto the fluorescent surface below and will excite this surface to fluorescence. The fluorescent light can pass the indicator filter. Thus the indicator area 75 appears blue in the recorded image upon illumination by a PDD illumination spectrum and observation by a PDD observation filter and green to red upon illumination with an AF illumination spectrum and observation by an AF observation spectrum.

If a video camera 31 is used that permits it, the illumination time or the amplification can be firmly specified before recording the image and only the other parameter that is entered in each case can be recorded and evaluated. Thereby it becomes possible to distinguish and to identify, for example, a combination of a PDD illumination spectrum with an AF observation filter (compare curve 85 in FIG. 5) and a combination of an AF illumination spectrum with a PDD observation filter (compare curve 86 in FIG. 5) through an at lest semiquantitative evaluation of the brightness of a white area of the reference surface 72 in the recorded image.

In the framework of the described test method, in particular by a user interface, patient data can be recorded and then filed in a database along with the result of the test method and in particular with the result of an ensuing examination of the patient by means of the optic investigation system. This ensures that the optic investigation system before or after the examination of a patient is tested for its functionality and that the result of this test is logged or documented.

FIG. 7 shows a schematic flow diagram of a method for testing an optic investigation system with a light source, an imaging device and a video camera for optical investigation of an object. Although the method is applicable also in optic investigation systems and test apparatuses that differ from the one presented above with reference to FIGS. 1 and 2, hereafter for the sake of simplicity of understanding, reference numbers from FIGS. 1 and 2 are used by way of example. The method can include characteristics of the test method described above and of its described variants. In particular, the method can be a combination of several described variants.

In an optional first step 101, a distal end 12 of an imaging device 10, in particular of an endoscope, is introduced through an aperture 43 into a hollow space 42 in a light-insulated housing 41. In an optional second step 102, which can be executed immediately after the first step 101 or simultaneously with it, the distal end 12 of the imaging device 10 is positioned in a predetermined position and direction in relation to a reference surface 72 positioned in the hollow space 42. This occurs, for example, with the support of a positioning device 50, which guides the imaging device 10, in particular its distal end 12, and/or holds it by form- or force-locking.

Alternatively, the following steps are executed without first introducing the distal end 12 of the imaging device 10 into a hollow space 42 and/or without first exactly positioning the distal end 12 of the imaging device 10.

In a third step 103, the reference surface 72 is illuminated with illuminating light with an illumination spectrum. If the imaging device is an endoscope 10, the illumination occurs in particular by means of the endoscope 10 or by means of an illumination beam path in the endoscope 10.

If a video camera 31 is used, in an optional fourth step 104 a white balance can be executed while the reference surface is illuminated. In the process, white balance parameters, for example WBG, WBY, are selected. If a camera 31 is used, in an optional fifth step 105 an operating condition of the camera 31 is selected. For example, the illumination time, amplification or other parameters affecting the lighting, the optical-electric conversion and the digitizing of images are selected at predetermined values.

In a sixth step 106, during the illumination of the reference surface 72 by the imaging device 10, an image is recorded by a video camera 31 or in direct visual manner such as by the human eye. In the second case the fifth step 105, among other procedures, can be dispensed with.

In an optional seventh step 107, the image recorded in the sixth step 106 by means of the imaging device 10 is compared with a reference image, in particular with several reference images. In a likewise optional eighth step 108, in the image recorded in the sixth step 106 the appearance of an indicator area is compared with the appearance of a reference area.

If a video camera 31 is used, in an optional ninth step 109 an operating condition of the camera that exists during the sixth step 106 can be recorded. The operating condition existing during the recording of the image makes possible in its own right, or together with the recorded image, an at least semiquantitative statement, for example, on the brightness of the image generated by the imaging device 10 in the camera or of an area within this image. For example, an at least semiquantitative statement can be derived on the basis of the illumination time, the amplification and the brightness values in the recorded image with familiar properties of the reference surface 72 and a familiar positioning of the distal end 12 of the imaging device in relation to the reference surface 72. On this basis, for example, with the example presented with reference to FIG. 5 it is possible to distinguish whether a reliable filter combination or an unreliable filter combination is present.

In a tenth step 110, a determination is made as to which illumination spectrum and which transmission spectrum are present in the observation beam path, in particular which illumination filter and which observation filter are present. This information can be acquired in particular from the appearance of the indicator area in the recorded image, from the result of comparing the recorded image with a reference image (seventh step 107) and/or from the result of comparing the appearances of the indicator area and the reference area in the recorded image (eighth step 108). If the image was recorded with a video camera, the determination of the illumination spectrum and of the transmission spectrum in the observation beam path can be alternatively or additionally influenced by the white comparison parameters ascertained in the fourth step 104, the operating condition of the camera 31 selected in the fifth step 105, and/or the operating condition of the camera 31 recorded in the ninth step 109.

If the image was immediately visually recorded in the sixth step 106, then in an optional eleventh step, by means of a user interface, properties of the recorded image or the result of comparing the recorded image with one or more reference images can be called up and recorded and incorporated into a data processing device. If the image was recorded by a camera in the sixth step 106, the tenth step can be executed by an apparatus, in particular by a camera control unit 35 or by a computer. In this case the result of the tenth step can already be present in a form that makes the following steps possible.

In an optional twelfth step 112, a report is issued that can include a statement on the functionality (in particular, the reliable and correct combination of illumination filter and observation filter), on the filter used, or on the illumination spectrum and transmission spectrum in the observation beam path. In addition, the report can include an operating recommendation and/or an operating instruction. For example, the report can include an instruction to exchange the illumination filter for another illumination filter or the imaging device for another imaging device with a different transmission spectrum.

In an optional thirteenth step 113, which can also be executed at any other point in the method, patient data are recorded, for example by means of a user interface. In an optional fourteenth step 114, the patient data, the result of the test method and optionally the result of an ensuing or preceding examination of a patient by means of the optional investigation system are filed in a database.

In particular in using a video camera 31, in addition, model designations, series numbers, software or firmware versions and other data on components of the optic investigation system are queried over a communication line 39 and filed for documentation or logging in the database. In addition the investigation of the patient can be documented or logged in the database or separately on another data carrier. In the process, for example, images or a video data stream from the camera 31 is filed in the database (for example in an Mpeg format) or on videotape.

The invention claimed is:

1. A method for testing an optical investigation system, the method comprising the steps of:
providing a light source configured to generate illuminating light at least either with a first predetermined illumination spectrum or with a second predetermined illumination spectrum;
providing an imaging device for optical investigation of an object in remitted light and fluorescent light, the imaging device having a proximal end and a distal end and having an observation beam path that comprises at least either a first predetermined transmission spectrum or a second predetermined transmission spectrum;
providing an artificial test apparatus, the test apparatus comprising a light-insulated housing having an aperture at one end and being closed at the other end and including a hollow space within the light-insulated housing, the test apparatus having a reference body at the closed end of the test apparatus, the reference body including a reference surface, the reference surface having a reference area and an indicator area on the reference area, wherein the indicator area has a wavelength-dependent optical property that changes between a first focal point of the first predetermined illumination spectrum of the light source and the first predetermined transmission spectrum of the imaging device, and a second focal point of the second predetermined illumination spectrum of the light source and the second predetermined transmission spectrum of the imaging device;
positioning the distal end of the imaging device through the aperture and into the hollow space of the test apparatus by using a positioning device, the positioning device holding the imaging device by form-locking or force-fitting, in such a way that the distal end of the imaging device is positioned in a predetermined position and in a predetermined direction in the hollow space;
illuminating the reference surface with illuminating light from the light source;
recording an image of the reference surface by means of the imaging device; and
determining which illumination spectrum and which transmission spectrum was present in the observation beam path on recording the image, on the basis of the recorded image.

2. The method of claim 1, wherein the step of determining includes a comparison of the recorded image with a reference image.

3. The method of claim 1, wherein the step of determining includes a comparison of a reproduction of the indicator area with a reproduction of the reference area in the recorded image.

4. The method of claim 1, wherein an optical property of the indicator area and an optical property of a reference area on the reference surface mutually change one another between the first focal point and the second focal point.

5. The method of claim 4, wherein the indicator area includes an indicator filter whose filter edge lies between the first focal point and the second focal point.

6. The method of claim 5, wherein the indicator area includes a fluorescent surface behind the indicator filter.

7. The method of claim 1, wherein the image of the reference surface is recorded visually or by a video camera.

8. The method of claim 1, further comprising selecting an operating condition of a video camera at a predetermined value before recording the image of the reference surface by the camera.

9. The method of claim 1, further comprising recording an operating condition of the video camera existing during the recording of the image by a video camera.

10. The method of claim 1, further comprising recording patient data and filing information on the illumination spectrum and transmission spectrum in the observation beam path as well as the patient data in a database.

11. A system for testing an optic investigation system, the system comprising:
a light source to generate a first predetermined illumination spectrum or a second predetermined illumination spectrum;
an imaging device with an observation beam path with a first predetermined transmission spectrum or a second predetermined transmission spectrum; and
an artificial test apparatus, the test apparatus comprising:
a reference body located within the test apparatus, the reference body having a reference surface positioned in a hollow space of the test apparatus, the reference surface having a reference area and an indicator area on the reference area, wherein the indicator area has a wavelength-dependent optical property that changes between a first focal point of the first predetermined illumination spectrum of the light source and the first predetermined transmission spectrum of the imaging device, and a second focal point of the second predetermined illumination spectrum of the light source and the second predetermined transmission spectrum of the imaging device;
a positioning device that holds the imaging device by form-locking or force-fitting, in such a way that the distal end of the imaging device is positioned in a predetermined position and in a predetermined direction in the hollow space of the test apparatus.

12. A system for testing an optical investigation system, the system being configured to execute a method for testing an optical investigation system with a light source configured to generate illuminating light at least either with a first predetermined illumination spectrum or with a second predetermined illumination spectrum and an imaging device for optical investigation of an object in remitted light and fluorescent light the imaging device having an observation beam path that comprises at least either a first predetermined transmission spectrum or a second predetermined transmission spectrum, the method comprising:

positioning the distal end of the imaging device within an artificial test apparatus having a light-insulated housing and a hollow space located within the light-insulated housing and an aperture to the hollow space, the test apparatus having a reference body including a reference surface positioned in the hollow space, such that the distal end of the imaging device is positioned through the aperture into the hollow space by a positioning device that holds the imaging device by form-locking or force-fitting, in such a way that the distal end of the imaging device is positioned in a predetermined position and in a predetermined direction in the hollow space of the test apparatus;

illuminating the reference surface with illuminating light from the light source;

recording an image of the reference surface by means of the imaging device; and determining which illumination spectrum and which transmission spectrum was present in the observation beam path on recording the image, on the basis of the recorded image.

13. The method of claim 1, wherein the reference surface has the spatial shape of a portion of a spherical surface or of a cylindrical mantle.

14. The system of claim 11, wherein the reference surface has the spatial shape of a portion of a spherical surface or of a cylindrical mantle.

15. The system of claim 12, wherein the reference surface has the spatial shape of a portion of a spherical surface or of a cylindrical mantle.

16. The system of claim 12, wherein the positioning device prevents penetration of light into the hollow space in the housing.

17. The method system of claim 12, wherein a mechanical stop or a catch-locking connection is used for form-locking or force-fitting the imaging device.

18. The system of claim 11, wherein the positioning device prevents penetration of light into the hollow space in the housing.

19. The system of claim 11, wherein a mechanical stop or a catch-locking connection is used for form-locking or force-fitting the imaging device.

20. The system of claim 11, wherein the reference body is made of polytetrafluoroethylene PTFE or of silicon.

21. The system of claim 12, wherein the reference body is made of polytetrafluoroethylene PTFE or of silicon.

22. The method of claim 1, further comprising performing a white balance.

23. The method of claim 1, wherein the method for testing an optical investigation system further includes the steps of:

performing a white balance;

selecting an operating condition of a video camera at a predetermined value before recording the image of the reference surface by the camera;

comparing the recorded image with a reference image;

comparing a reproduction of the indicator area with a reproduction of the reference area in the recorded image; and recording the operating condition of the video camera existing during the recording of the image by a video camera.

* * * * *